(12) United States Patent
Ijasan et al.

(10) Patent No.: US 11,852,013 B2
(45) Date of Patent: Dec. 26, 2023

(54) IDENTIFYING FLUID TYPES AND ASSOCIATED VOLUMES IN ROCK SAMPLES USING NUCLEAR MAGNETIC RESONANCE ANALYSES

(71) Applicant: ExxonMobil Technology and Engineering Company, Spring, TX (US)

(72) Inventors: Olabode Ijasan, The Woodlands, TX (US); Darren M. McLendon, Houston, TX (US)

(73) Assignee: ExxonMobil Technology and Engineering Company, Spring, TX (US)

( * ) Notice: Subject to any disclaimer, the term of this patent is extended or adjusted under 35 U.S.C. 154(b) by 395 days.

(21) Appl. No.: 16/947,762

(22) Filed: Aug. 14, 2020

(65) Prior Publication Data
US 2021/0131282 A1 May 6, 2021

Related U.S. Application Data

(60) Provisional application No. 62/930,275, filed on Nov. 4, 2019, provisional application No. 62/930,270, filed on Nov. 4, 2019.

(51) Int. Cl.
*E21B 49/08* (2006.01)
*E21B 49/02* (2006.01)
(Continued)

(52) U.S. Cl.
CPC ............ *E21B 49/088* (2013.01); *E21B 7/046* (2013.01); *E21B 49/02* (2013.01);
(Continued)

(58) Field of Classification Search
CPC .... E21B 49/088; E21B 49/02; E21B 49/0875; E21B 7/046; G01N 15/088;
(Continued)

(56) References Cited

U.S. PATENT DOCUMENTS

2011/0307438 A1* 12/2011 Martinez .................. G06N 5/00
706/52
2012/0065888 A1* 3/2012 Wu .......................... G06F 19/00
702/8

(Continued)

OTHER PUBLICATIONS

Anand, V. et al. (2017) "Unlocking the Potential of Unconventional Reservoirs Through New Generation NMR T1/T2 Logging Measurements Integrated with Advanced Wireline Logs", Petrophysics, vol. 58, No. 2, pp. 81-96.

(Continued)

*Primary Examiner* — Catherine T. Rastovski
*Assistant Examiner* — Lal C Mang
(74) *Attorney, Agent, or Firm* — ExxonMobil Technology and Engineering Company—Law Department

(57) ABSTRACT

A method for partitioning NMR $T_1$-$T_2$ data may comprise: identifying modes in NMR $T_1$-$T_2$ data from a plurality of samples with a multimodal deconvolution or decomposition with regularized nonlinear inversion; deriving a modal properties vector comprising modal properties for each of the modes; performing a cluster analysis of the modes to identify clusters; assigning a poro-fluid class to the clusters based on one or more of the modal properties of the modes in each of the clusters; and deriving partitioned representations for the clusters based on the cluster analysis.

14 Claims, 8 Drawing Sheets

(51) Int. Cl.
G01N 24/08 (2006.01)
G01V 3/32 (2006.01)
G01V 3/38 (2006.01)
E21B 7/04 (2006.01)
G01N 33/24 (2006.01)
G01R 33/50 (2006.01)
G01N 15/08 (2006.01)

(52) U.S. Cl.
CPC ....... *E21B 49/0875* (2020.05); *G01N 15/088* (2013.01); *G01N 24/081* (2013.01); *G01N 24/082* (2013.01); *G01N 33/241* (2013.01); *G01R 33/50* (2013.01); *G01V 3/32* (2013.01); *G01V 3/38* (2013.01); *G01N 2015/0846* (2013.01)

(58) Field of Classification Search
CPC .. G01N 24/081; G01N 24/082; G01N 33/241; G01N 2015/0846; G01R 33/50; G01R 33/448; G01V 3/32; G01V 3/38; G01V 3/14
See application file for complete search history.

(56) References Cited

U.S. PATENT DOCUMENTS

2016/0131628 A1* 5/2016 Fontenelle .............. G01N 33/24
2017/0003411 A1* 1/2017 Chok ................... G01R 33/448

OTHER PUBLICATIONS

Brownstein, K. R. et al. (1979) "Importance of Classical Diffusion in NMR Studies of Water in Biological Cells", Physica Review A, vol. 19, No. 6, pp. 2446-2453.

Hirasaki, G. J. et al. (2003) "NMR Properties of Petroleum Reservoir Fluids", Magnetic Resonance Imaging, vol. 21, No. 3-4, pp. 269-277.

Ijasan, O. et al. (2020) "Estimating Characteristic Relaxation Properties from NMR T1-T2 Measurements in Unconventional Reservoirs", Unconventional Resources Technology Conference, Jul. 20-22, 2020 (URTEC-2020-3346-MS), pp. 1-18.

Kausik, R. et al. (2016) "NMR Relaxometry in Shale and Implications for Logging", Petrophysics, vol. 57, No. 4, pp. 339-350.

Kenyon, W. E. (1997) "Petrophysical Principles of Applications of NMR Logging", The Log Analyst, vol. 38, No. 2, pp. 21-43.

Nelson, P. H. (1994) "Permeability Porosity Relationships in Sedimentary Rocks", The Log Analyst, vol. 35, No. 3, pp. 38-62.

Venkataramanan, L. et al. (2018) "An Unsupervised Learning Algorithm to Compute Fluid Volumes from NMR T1-T2 Logs in Unconventional Reservoirs", Petrophysics, vol. 59, No. 5 (Oct. 2018), pp. 617-632; Originally presented as Transactions of the Society of Petrophysicists and Well Log Analysts, 59th Annual Logging Symposium, London, UK, Jun. 2-6, 2018, Paper Y.

Xie, H. et al. (2019) "Investigation of Physical Properties of Hydrocarbons in Unconventional Mudstones Using Two- Dimensional NMR Relaxometry", Transactions of the Society of Petrophysicists and Well Log Analysts, 60th Annual Logging Symposium, Jun. 15-19, 2019, pp. 1-10.

Ye, S. et al. (2019) "Method of Determining Unconventional Reservoir Saturation with NMR Logging", Society of Petroleum Engineers Annual Technical Conference and Exhibition, SPE-196069-MS, pp. 1-15.

Aster, R. C. et al. (2005a) "Tikhonov Regularization", Parameter Estimation and Inverse Problems, vol. 90, pp. 89-118.

Aster, R. C. et al. (2005b) "Nonlinear Regression", Parameter Estimation and Inverse Problems, vol. 90, pp. 171-199.

Hansen, P. C. (2010a) "Computational Aspects: Regularization Methods", Discrete Inverse Problems: Insights and Algorithms, Society of Industrial and Applied Mathematics, Monographs on Fundamentals of Algorithms, pp. 53-79.

Hansen, P. C. (2010b) "Getting Serious: Choosing the Regularization Parameter", Discrete Inverse Problems: Insights and Algorithms, Society of Industrial and Applied Mathematics, Monographs on Fundamentals of Algorithms, pp. 85-105.

Chen, S., et al. (2016) "New Approaches of 3D Nuclear Magnetic Resonance Inversion for Improving Fluid Typing", Interpretation, vol. 4, No. 2. May 1, 2016, pp. SF67-SF79, XP055742789.

Doveton, J. et al. (2015) "Textural and Pore Size Analysis of Carbonates from Integrated Core and Nuclear Magnetic Resonance Logging: An Arbuckle Study", Interpretation, vol. 3, No. 1, Feb. 1, 2015, pp. SA77-SA89, XP055742319.

Jiang, H. et al. (2019) "A Comparison of Clustering Algorithms Applied to Fluid Characterization Using NMR T1-T2 Maps of Shale", Computers & Geosciences, vol. 126, Feb. 2, 2019, pp. 52-61, XP055742289.

Venkataramanan, L. et al. (2002) "Solving Fredholm Integrals of the First Kind with Tensor Product Structure in 2 and 2.5 Dimensions", IEEE Transactions on Signal Processing, vol. 50, No. 5, May 1, 2002, pp. 1017-1026, XP055742786.

* cited by examiner

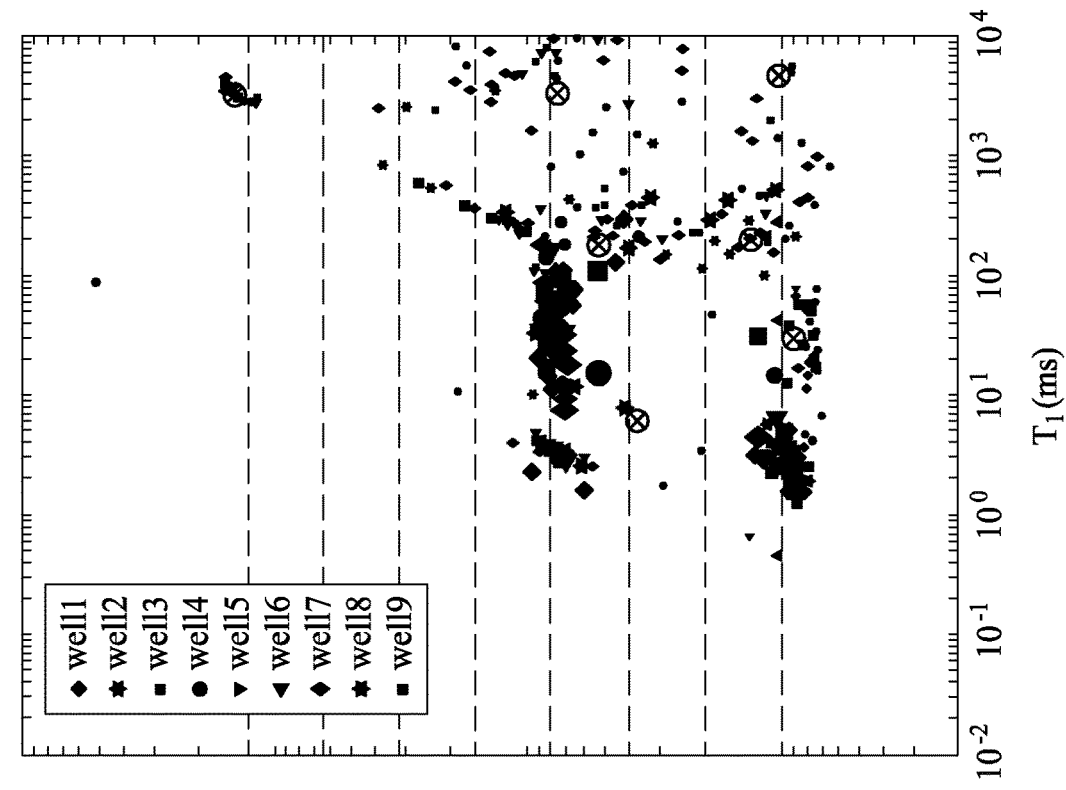
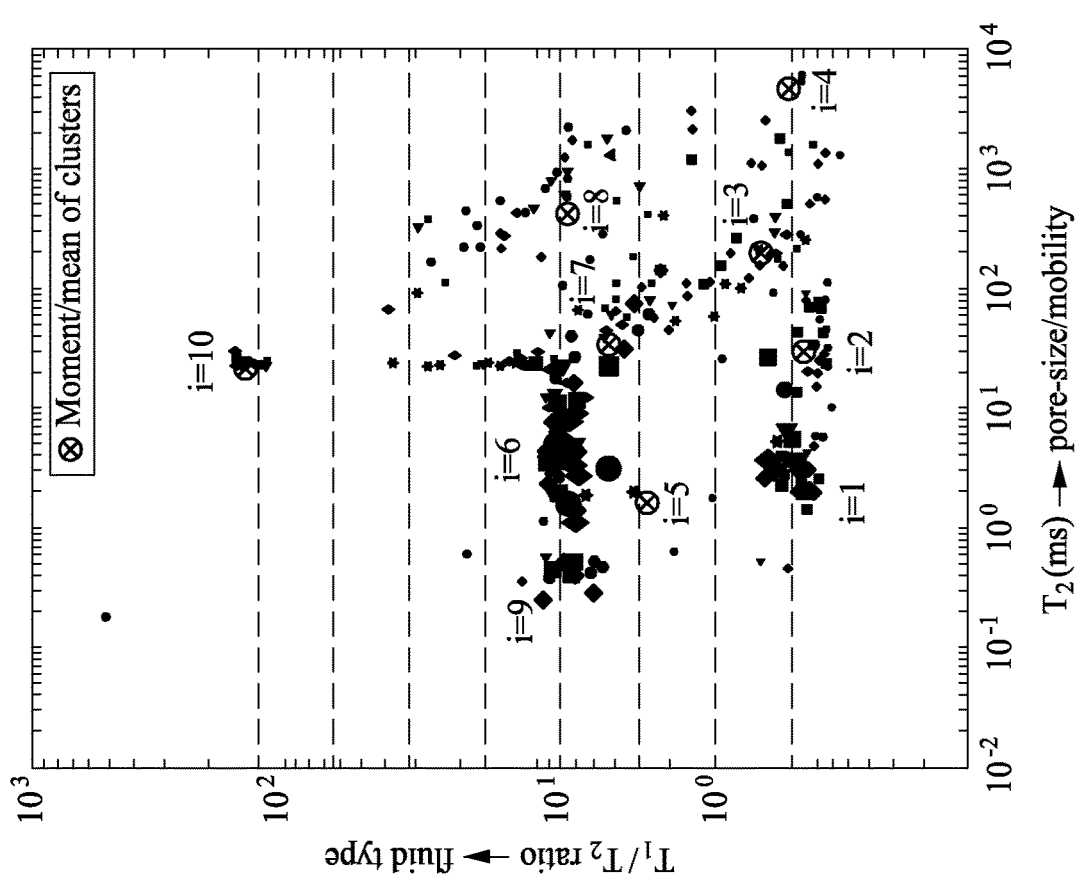
FIG. 3(A)
FIG. 3(B)

IDENTIFYING FLUID TYPES AND ASSOCIATED VOLUMES IN ROCK SAMPLES USING NUCLEAR MAGNETIC RESONANCE ANALYSES

CROSS REFERENCE TO RELATED APPLICATIONS

This application claims the priority benefit of U.S. Provisional Application No. 62/930,270 filed Nov. 4, 2019 and U.S. Provisional Application No. 62/930,275 filed Nov. 4, 2019, the disclosures of which are incorporated herein by reference in their entirety.

BACKGROUND

The present disclosure relates to nuclear magnetic resonance (NMR) analyses for identifying the types of fluids and associated volumes in subterranean formations via core rock samples and/or borehole logging techniques.

During oil and gas exploration, zones with higher concentrations of oil and gas can be identified as target zones. One method of identifying target zones is using NMR analysis with core rock samples and/or borehole logging techniques.

One such NMR technique is to analyze a two-dimensional NMR cross-plot, specifically of the longitudinal relaxation time ($T_1$) versus the transverse relaxation time ($T_2$). The sum of the NMR signal amplitude over the $T_1$-$T_2$ cross-plot is proportional to the total fluid-filled porosity of the sample for which the NMR measurements were performed. A more detailed analysis of the $T_1$-$T_2$ cross-plot can be performed using polygonal partitioning, which is the most common industry practice for detailed interpretation of $T_1$-$T_2$ cross-plots. That is, portions of the $T_1$-$T_2$ cross-plot are partitioned and assigned a fluid type (e.g., water, gas, or oil). The sum of the NMR signal amplitude over individual partitions is proportional to the volume of the assigned fluid in the sample, for example, as described in (a) Kausik, R., Fellah, K., Rylander, E., Singer, P. M., Lewis, R. E., and Sinclair, S. M., 2016, NMR relaxometry in shale and implications for logging: Petrophysics, 57, no. 4, 339-350, (b) Xie, Z. H., and Gan, Z., 2019, Investigation of physical properties of hydrocarbons in unconventional mudstones using two-dimensional NMR relaxometry: Transactions of the Society of Petrophysicists and Well Log Analysts, 60th Annual Logging Symposium, and (c) Ye, S., Scribner, A., McLendon, D., Ijasan, O., Chen, S., Shao, W., and Balliet, R., 2019, Method of determining unconventional reservoir saturation with NMR logging: Society of Petroleum Engineers Annual Technical Conference and Exhibition, SPE 196069.

Other techniques assume linear combinations of a priori known fluid sources that may be blindly separated, for example, as described in Anand, V., Ali, M. R., Abubakar, A., Grover, R., Neto, O., Pirie, I., and Iglesias, J. G., 2017, Unlocking the potential of unconventional reservoirs through new generation NMR $T_1/T_2$ logging measurements integrated with advanced wireline logs: Petrophysics, 58, no. 2, 81-96.

However, the $T_1$ and $T_2$ values associated with a fluid can vary based on the type of rock (e.g., shale, sandstone, carbonates, and the like), fluid composition (gaseous or liquid), and NMR frequency (low or high field); so the partitions for one rock and measurement type may differ from another rock and measurement type.

There are several tools that can be used to perform polygonal partitioning where the approaches to defining the polygons to partition the $T_1$-$T_2$ cross-plot vary widely, for example as described in Venkataramanan, L., Evirgen, N., Allen, D. F., Mutina, A., Cai, Q., Johnson, A. C., Green, A. Y., Jiang, T., 2018, An unsupervised learning algorithm to compute fluid volumes from NMR $T_1$-$T_2$ logs in unconventional reservoirs: Transactions of the Society of Petrophysicists and Well Log Analysts, 59th Annual Logging Symposium. Further, the person using the tools to analyze the $T_1$-$T_2$ cross-plot typically has a good deal of control over the partition boundaries, in part because partitions can vary based on rock type. This user control makes what appear to be systematic tools more subjective. These tools also do not account for any overlapping signals from different fluids. Accordingly, the state-of-the-art tools for a widely used analysis technique (polygonal partitioning of $T_1$-$T_2$ cross-plots) used to identify target zones can be tedious and inaccurate.

SUMMARY OF THE INVENTION

The present disclosure relates to NMR $T_1$-$T_2$ cross-plot analyses (referred to herein as a NMR petrophysical pore multimodal (NPPM) analysis) for identifying the types of fluids and associated volumes in subterranean formations.

A method of the present disclosure comprises: identifying modes in NMR $T_1$-$T_2$ data from a plurality of samples with a multimodal deconvolution or decomposition with regularized nonlinear inversion; deriving a modal properties vector comprising modal properties for each of the modes; performing a cluster analysis of the modes to identify clusters; assigning a poro-fluid class to the clusters based on one or more of the modal properties of the modes in each of the clusters; and deriving partitioned representations for the clusters based on the cluster analysis.

A computing device of the present disclosure comprises: a processor; a memory coupled to the processor; and instructions provided to the memory, wherein the instructions are executable by the processor to perform the method according to the foregoing method.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

FIG. 2(H) is the fractional saturation or relative percentages of modal pore volumes with respect to total fluid-filled volume.

FIGS. 3(A)-3(B) are the overlaid data from several samples plotted as $T_1/T_2$ ratio as a function of $T_2$ and $T_1$ with cluster associations and moments.

FIGS. 4(A)-3(B) are the partitioned area of $T_1/T_2$ ratio as a function of $T_2$ and $T_1$.

DETAILED DESCRIPTION

Figure 1:
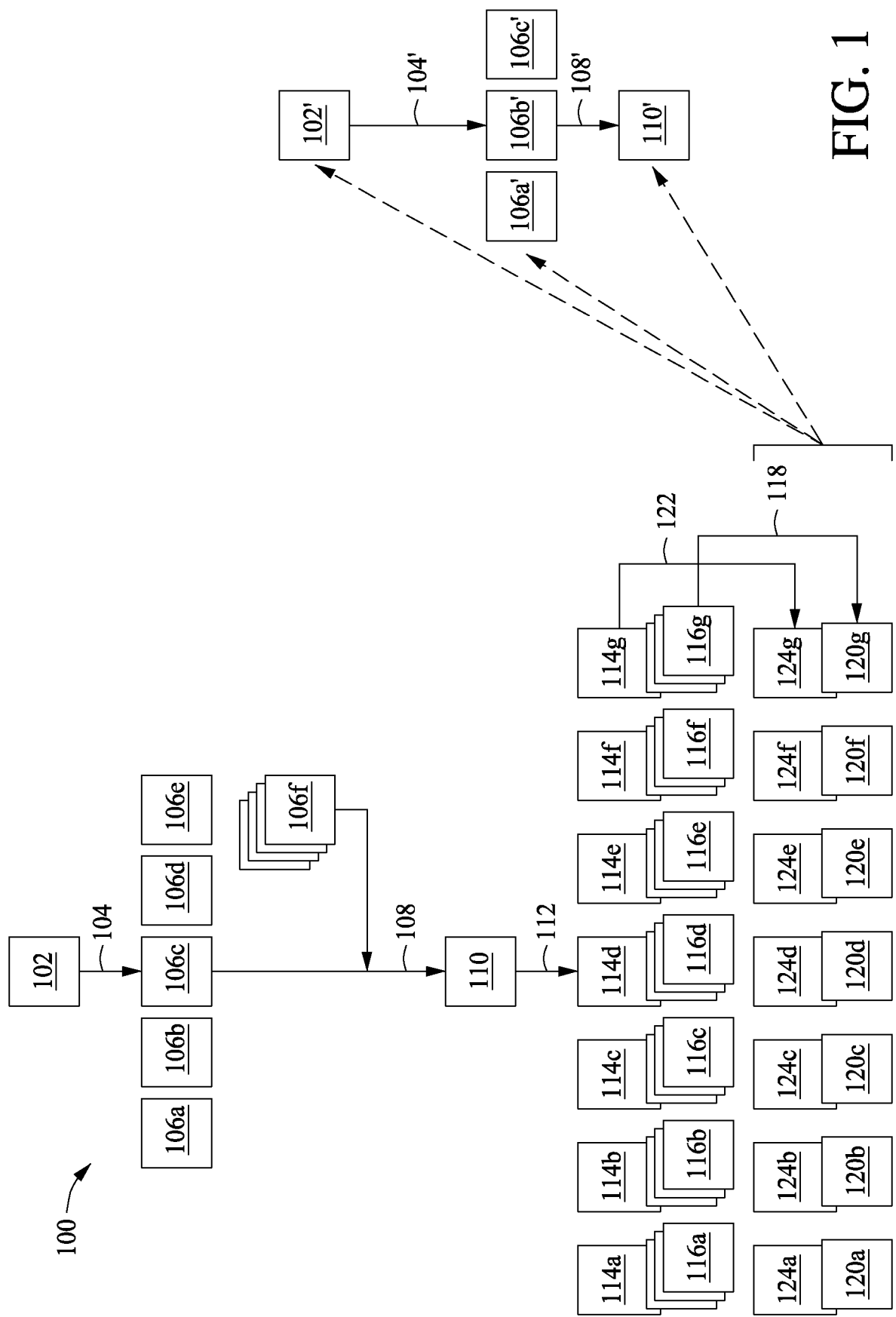
FIG. 1 is a diagram of a nonlimiting example method of the present disclosure.

The present disclosure relates to NMR analyses for identifying the types of fluids (poro-fluid classes) and associated volumes in subterranean formations using core samples and/or logging techniques. More specifically, the methods and systems of the present disclosure use a novel NMR petrophysical pore multimodal (NPPM) analysis to (a) analyze the NMR $T_1$-$T_2$ data (e.g., $T_1$-$T_2$ cross-plots and other plots) of fluid in several rock samples (e.g., a core sample from a subterranean formation and/or a portion of rock in the subterranean formation and/or a synthetic core sample) to identify modes (or peaks) in the NMR $T_1$-$T_2$ data, (b) identify clusters of modes and associating said clusters with fluid-types in specific pore-sizes (referred to herein as poro-fluid class), and (c) deriving partitioned representations for the poro-fluid classes (e.g., equations, regions, regimes, and partition lines or the like that define the boundaries of poro-fluid classes). Then, additional rock samples can be analyzed using said partitioned representations to identify the amount of each poro-fluid class in the newly acquired $T_1$-$T_2$ cross-plots. This unique approach to $T_1$-$T_2$ cross-plot analysis is rooted in statistical data analytics, which greatly mitigates user subjectivity and improves the accuracy of the NPPM analysis technique over other commonly used techniques. Further, because the disclosed analysis technique is based on data and NMR principles, the NPPM analysis technique is robustly applicable to a variety of rock samples without introducing significant, if any, subjectivity.

The $T_1$-$T_2$ cross-plots and $T_1$-$T_2$ cross-plot representations are used generically to describe a plot or mathematical representation thereof (e.g., table, series of mathematical equations, or the like) of a measure of the NMR signal amplitude (e.g., A or any mathematical manipulation of A) as a function of a measure of $T_1$ (e.g., absolute value of $T_1$, $\log_{10} T_1$, or any other mathematical manipulation of $T_1$) and a measure of $T_2$ (e.g., absolute value of $T_2$, $\log_{10} T_2$, or any other mathematical manipulation of $T_2$). $T_1$-$T_2$ cross-plots can be 2-dimensional or 3-dimensional plot. 2-dimensional plots typically have the measure of $T_1$ and the measure of $T_2$ are the y- and x-axes (in either configuration) and the measure of amplitude represented with contours or colors, for example, in the 2-dimensional space. Other plots and plot representations described herein are similarly a plot or mathematical representation thereof.

The NPPM analysis technique described herein derives the partitioned representations for the poro-fluid classes using a two-part analysis of NMR $T_1$-$T_2$ data from several rock samples. Preferably, but not necessarily, said rock samples are from the same or similar types of rock to reduce ambiguity introduced from different fluid-rock interactions that affect $T_1$ and/or $T_2$ data.

In a first part, the NMR $T_1$-$T_2$ data (e.g., as $T_1$-$T_2$ cross-plots and other plots) undergo a multimodal deconvolution or decomposition achieved by regularized nonlinear inversion. The use of an inversion solves for mixtures of multiple modes (or peaks in the data and/or $T_1$-$T_2$ cross-plot) and their decomposed peak shape basic functions. The result is a modal properties vector that mathematically describes each of the modes in the NMR $T_1$-$T_2$ data. Said modal properties vectors (one, some, or all from each individual set of the NMR $T_1$-$T_2$ data) can optionally be plotted, for example, as a $T_1$-$T_2$ cross-plot representation and other plot representation, which are both approximations of the actual $T_1$-$T_2$ cross-plot or other plot.

The use of the regularized nonlinear inversion with the multimodal deconvolution or decomposition enables a fast convergence to a suitable modal properties vector for each mode or poro-fluid type, without the need for a priori known database of fluid types or sources.

The modal properties vector is a mathematical representation of the poro-fluid modal properties for a given mode, or all present modes. Examples of poro-fluid modal properties include, but are not limited to, amplitude, pore volume, peak $T_1$, peak $T_2$, peak $T_1/T_2$ ratio, shape covariance matrix, Jacobian derivative functions, uncertainty, convergence, and inversion analytics, and the like, and any combination thereof. The absolute values of poro-fluid modal properties can be analyzed. Additionally, the modes can be represented on plots of peak $T_1/T_2$ ratio as a function of peak $T_1$ and peak $T_1/T_2$ ratio as a function of peak $T_2$ for analysis, or any plot of any of the modal properties. The $T_1/T_2$ ratio may relate to the fluid type, the $T_2$ relaxation time may relate to the pore size and mobility of the fluid, and $T_1$ relaxation time may relate to fluid type, rock wettability, or NMR activation sequence.

The volume of fluid for each mode is the modal pore volume and the fractional saturation of fluid for each mode can be derived from the modal pore volume relative to total fluid-filled porosity of sample.

A peak amplitude threshold value (e.g., absolute value, minimum percentage of peak amplitude of the $T_1$-$T_2$ cross-plot, and the like) can be used to automatically define the presence or absence of a mode in a local maxima and inflections. Alternatively, the number of modes can be defined by the user.

The modes of the $T_1$ and $T_2$ NMR data (e.g., the $T_1$-$T_2$ cross-plots or other plots) can be deconvolved or decomposed using any variety of peak shape basis functions. Examples of peak shape basis functions include, but are not limited to, Gaussian, Lorentzian, Voigt, exponentially modified Gaussian, and the like, and any variation thereof. A preferred peak shape basis function is Gaussian because it tends to better describe geologic processes and produce better conformed peak shape basic functions.

The regularized nonlinear inversion can be performed by any suitable techniques including, but not limited to, Gauss-Newton inversion, Landweber inversion, Levenberg-Marquartz inversion, Occam's inversion, and the like, and any variation thereof. A preferred regularized nonlinear inversion technique is Levenberg-Marquartz inversion. Regularized nonlinear inversion is described in Aster, R. C., Borchers, B., and Thurber, C. H., 2005, Parameter estimation and inverse problems: Elsevier and Hansen, P. C., 2010, Discrete inverse problems: Insights and algorithms: Society of Industrial and Applied Mathematics, Monographs on Fundamentals of Algorithms.

Once the modes are identified and deconvolved or decomposed to modal properties vectors or other suitable mathematical representation for the NMR $T_1$-$T_2$ data of a plurality of samples, the modes for the plurality of samples are analyzed as a whole by cluster analysis to identify clusters of modes, where a cluster may include one or more poro-fluid classes. Once the clusters are identified, the poro-fluid modal properties for each mode in each cluster are used to assign a fluid type to the cluster. The modal properties are used to identify the fluid-type because the modal properties describe the dominant magnetic resonance relaxation of the poro-fluid signature. One skilled in the art without undo experimentation will recognize how to identify a poro-fluid class based on absolute values of the poro-fluid modal properties.

After the $T_1$-$T_2$ data for several samples have been analyzed, a cluster analysis of the poro-fluid modal properties (e.g., peak $T_1$, peak $T_2$, pore volume, shape covariance, and the like, and any combination thereof) of modes of several samples can be performed to identify the regions, regimes, and boundaries of each poro-fluid class. For example, the data from several samples can be overlaid on the $T_1$-$T_2$ cross-plot, plots of peak $T_1/T_2$ ratio as a function of peak $T_1$ and peak $T_1/T_2$ ratio as a function of peak $T_2$, or other plot, and cluster analysis can be performed to identify the suitable boundaries to define each poro-fluid class. The representation of these boundaries is referred to herein as a partitioned representation, which is any mathematical or pictorial representation of the boundaries within the T i-$T_2$ data space (e.g., the $T_1$-$T_2$ cross-plot, plots of peak $T_1/T_2$ ratio as a function of peak $T_1$ and peak $T_1/T_2$ ratio as a function of peak $T_2$, or other plot) for each poro-fluid class are derived. Preferably, the cluster analysis is performed on the plots of peak $T_1/T_2$ ratio as a function of peak $T_1$ and peak $T_1/T_2$ ratio as a function of peak $T_2$ because the individual modes have less overlap when plotted. Preferably, the cluster analysis is performed on any of the modal properties of the multimodal deconvolution or decomposition.

The cluster analysis can be performed, for example, with partitioning algorithms, hierarch algorithms, density-based algorithms, grid-based algorithms, graph-based algorithms, and the like, and any combination thereof. One skilled in the art without undo experimentation will recognize how to identify a poro-fluid class based on values of means, weighted-means, or moments of poro-fluid modal properties within the same cluster.

Examples of poro-fluid classes include, but are not limited to, free fluid, fluid in pores, fluid in macroporosity or fractures, fluid in inorganic pores, fluid in organic pores, free liquid, liquid in pores, liquid in macroporosity or fractures, liquid in inorganic pores, liquid in organic pores, free gas, gas in pores, gas in macroporosity or fractures, gas in inorganic pores, gas in organic pores, free oil, oil in pores, oil in macroporosity or fractures, oil in inorganic pores, oil in organic pores, free water, water in pores, water in macroporosity or fractures, water in inorganic pores, water in organic pores, clay-associated water, clay-bound water, surface relaxation-dominated fluid, surface relaxation-dominated oil, surface relaxation-dominated water, bulk relaxation-dominated fluid, bulk relaxation-dominated oil, bulk relaxation-dominated water, bulk relaxation-dominated gas, bound fluid, bound oil, bound water, capillary-bound fluid, capillary-bound water, capillary-bound oil, bitumen, free hydrocarbon, bound hydrocarbon, and the like, and any combination thereof.

While an advantage of the NPPM analysis described herein is the ability to deconvolved and identify each component mode present in the NMR $T_1$-$T_2$ data, a user can determine a desired level of granularity in poro-fluid class definition by the NPPM analysis. For example, two modes may overlap and the user may opt to identify the two overlapping modes as one poro-fluid class or two poro-fluid classes. For example, in the Examples Section herein, mode 4 and mode 5 have some overlap and are associated with water in inorganic pores and oil in inorganic pores, respectively. In the example, these modes are identified with different poro-fluid classes. Optionally, a user could just be interested in fluid in inorganic pores and consider these modes together when identifying a poro-fluid class for one or more modes.

In another example, a user can decide that only five poro-fluid classes (e.g., free oil, free water, oil in pores, water in pores, and other fluids) are of interest. Accordingly, if the NMR $T_1$-$T_2$ data has more than five modes, more than one mode (overlapping or not) may be assigned to a poro-fluid class.

FIG. 1 is a diagram of a nonlimiting example method 100 of the present disclosure. First, NMR data 102 is collected for a fluid in a rock sample or rock volume (e.g., a core sample from a subterranean formation and/or a portion of rock in the subterranean formation and/or a synthetic core sample) and optionally analyzed to produce a $T_1$-$T_2$ cross-plot. The data 102 or plot derived therefrom undergoes a multimodal deconvolution or decomposition with regularized nonlinear inversion 104 to produce a modal properties vector 106a-e for all modes in the rock sample or volume. While five modes are illustrated, any number of modes (e.g., one to twelve or more) can be identified and analyzed.

The modal properties vector 106a-106e and associated modal properties are then combined 108 with modal properties vectors 106f from other samples to yield a plurality of modal property vectors 110 for a plurality of samples. Cluster analysis 112 is then performed on the plurality of modal property vectors 110 to identify clusters 114a-114g each having associated therewith a plurality of modal properties vectors 116a-116g. While seven clusters are illustrated, any number of clusters (e.g., one to twelve or more) can be identified and analyzed. The number of modes for an individual sample and clusters derived from the plurality of samples may be different because the modes corresponding to each cluster may not be present in every sample.

The one or more of the modal properties in the plurality of modal properties vectors 116a-116g for each cluster 114a-114g are then analyzed 118 to identify the poro-fluid class 120a-120g associated with the cluster 114a-114g. Further, the boundaries of the clusters 114a-114g are analyzed 122 to derive the partitioned representations 124a-124g for each of the clusters 114a-114g. The partitioned representations 124a-124g and the poro-fluid class 120a-120g can then be used for analyzing newly acquired NMR $T_1$-$T_2$ data or a derivation thereof.

For example, additional NMR data 102' (e.g., as raw data or a plot derived therefrom) collected from rock samples or rock volumes can optionally be similarly processed 104' to produce one or more modal properties vector 106a'-106c' and optionally further combined/processed 108' to produce a representation 110' of the additional NMR data 102'.

Depending on the level of treatment of the newly acquired NMR data 102', the newly acquired NMR data 102', the one or more modal properties vector 106a'-106c', and/or the representation 110' of the additional NMR data 102' can be compared to the partitioned representations 124a-124g to identify the poro-fluid class 120a-120g of modes within the newly acquired NMR data 102'.

For example, the partitioned representations 124a-124g may be partitioned areas on plots of peak $T_1/T_2$ ratio as a function of peak $T_1$ and peak $T_1/T_2$ ratio as a function of peak $T_2$. Then, partitioned areas of said plots can be used to identify the fluid types and poro-fluid classes of the newly acquired NMR data 102' plotted as peak $T_1/T_2$ ratio as a function of peak $T_1$ and peak $T_1/T_2$ ratio as a function of peak $T_2$. The amplitude and modal properties of the modes can be used to determine the volume of fluid for each mode, and consequently, each poro-fluid class in the newly acquired NMR data 102'.

The methods described herein can be used to analyze the fluid composition of subterranean formations (e.g., either using NMR logging data or analyzing core samples from the formation). The fluid compositional analysis can be used for identifying a zone of a subterranean formation for completion, identifying where to get a core sample for further analysis, identifying a horizontal well landing location, and/or determining a stimulation and/or completion operation.

Advantageously, because the multimodal decomposition with regularized nonlinear inversion is fast, the analyses described herein can be performed in the field to analyze real-time NMR data collected, for example, in a logging operation.

Various aspects of the systems and methods described herein utilize computer systems. Such systems and methods can include a non-transitory computer readable medium containing instructions that, when implemented, cause one or more processors to carry out the methods described herein.

"Computer-readable medium" or "non-transitory, computer-readable medium," as used herein, refers to any non-transitory storage and/or transmission medium that participates in providing instructions to a processor for execution. Such a medium may include, but is not limited to, non-volatile media and volatile media. Non-volatile media includes, for example, NVRAM, or magnetic or optical disks. Volatile media includes dynamic memory, such as main memory. Common forms of computer-readable media include, for example, a floppy disk, a flexible disk, a hard disk, an array of hard disks, a magnetic tape, or any other magnetic medium, magneto-optical medium, a CD-ROM, a holographic medium, any other optical medium, a RAM, a PROM, and EPROM, a FLASH-EPROM, a solid state medium like a memory card, any other memory chip or cartridge, or any other tangible medium from which a computer can read data or instructions. When the computer-readable media is configured as a database, it is to be understood that the database may be any type of database, such as relational, hierarchical, object-oriented, and/or the like. Accordingly, exemplary embodiments of the present systems and methods may be considered to include a tangible storage medium or tangible distribution medium and prior art-recognized equivalents and successor media, in which the software implementations embodying the present techniques are stored.

The methods described herein can, and in many embodiments must, be performed using computing devices or processor-based devices that include a processor; a memory coupled to the processor; and instructions provided to the memory, wherein the instructions are executable by the processor to perform the methods described herein (such computing or processor-based devices may be referred to generally by the shorthand "computer"). For example, any one or more of the following may be carried out using a computer: identifying modes in NMR $T_1$-$T_2$ data from a plurality of samples with a multimodal deconvolution or decomposition with regularized nonlinear inversion (although this may also be carried out manually, e.g., by observation); deriving a modal properties vector comprising modal properties for each of the modes; performing a cluster analysis of the modes to identify clusters; assigning a poro-fluid class to the clusters based on one or more of the modal properties of the modes in each of the clusters; and/or deriving partitioned representations for the clusters based on the cluster analysis. Similarly, any calculation, determination, or analysis recited as part of methods described herein will in may embodiments be carried out in whole or in part using a computer.

Furthermore, the instructions of such computing devices or processor-based devices can be a portion of code on a non-transitory computer readable medium. Any suitable processor-based device may be utilized for implementing all or a portion of embodiments of the present techniques, including without limitation personal computers, networks personal computers, laptop computers, computer workstations, mobile devices, multi-processor servers or workstations with (or without) shared memory, high performance computers, and the like. Moreover, embodiments may be implemented on application specific integrated circuits (ASICs) or very large scale integrated (VLSI) circuits.

The presently-described methods may all be deployed in managing hydrocarbons in the subterranean formation. As used herein, "managing hydrocarbons" or "hydrocarbon management" includes any one or more of the following: hydrocarbon extraction; hydrocarbon production, (e.g., drilling a well and prospecting for, and/or producing, hydrocarbons using the well; and/or, causing a well to be drilled, e.g., to prospect for hydrocarbons); hydrocarbon exploration; identifying potential hydrocarbon systems such as those including hydrocarbon-bearing formations; determining candidate-sampling locations within a hydrocarbon system; evaluating a hydrocarbon system; characterizing a hydrocarbon system such as a hydrocarbon-bearing formation; identifying well locations; determining well injection rates; determining well extraction rates; identifying reservoir connectivity; acquiring, disposing of, and/or abandoning hydrocarbon resources; reviewing prior hydrocarbon management decisions; and any other hydrocarbon-related acts or activities, such activities typically taking place with respect to a hydrocarbon system and/or subsurface formation. In particular embodiments, managing hydrocarbons may include one or more of identifying a zone of the subsurface formation for completion, and carrying out one or more completion operations on or in the identified zone; identifying a portion of the subterranean formation from where to obtain a core sample for further analysis, and obtaining one or more core samples from the identified portion; carrying out a simulation or completion operation on the subterranean formation; and/or identifying a horizontal well landing location within the subterranean formation and causing a horizontal well to be drilled to the identified landing location. The aforementioned broadly include not only the acts themselves (e.g., extraction, production, drilling a well, etc.), but also or instead the direction and/or causation of such acts (e.g., causing hydrocarbons to be extracted, causing hydrocarbons to be produced, causing a well to be drilled, causing the prospecting of hydrocarbons, etc.). Furthermore, methods may in particular include managing hydrocarbons based at least in part upon a determined relative concentration, abundance, and/or net NMR signal amplitude corresponding to the location of modes in or determined based at least in part on the derived partitioned representations.

Example Embodiments

A nonlimiting example embodiment of the present disclosure is a method comprising: identifying modes in NMR $T_1$-$T_2$ data from a plurality of samples with a multimodal deconvolution or decomposition with regularized nonlinear inversion; deriving a modal properties vector comprising modal properties for each of the modes; performing a cluster analysis of the modes to identify clusters; assigning a poro-fluid class to the clusters based on one or more of the modal properties of the modes in each of the clusters; and deriving partitioned representations for the clusters based on the cluster analysis. The nonlimiting example method embodiment can include one or more of the following: Element 1: wherein the multimodal deconvolution or decomposition is selected from the group consisting of Gaussian, Lorentzian, Voigt, exponentially modified Gaussian, and any variation thereof; Element 2: wherein the regularized nonlinear inversion is selected from the group consisting of Gauss-Newton inversion, Landweber inversion, Levenberg-Marquartz inversion, Occam's inversion, and any variation thereof; Element 3: wherein the nonlinear regularization inversion is an iterative calculation of multiple regularizations where the regularization in each iteration having a minimum misfit proceeds to the next iteration; Element 4: wherein the poro-fluid classes are selected from the group consisting of free fluid, fluid in pores, fluid in macroporosity or fractures, fluid in inorganic pores, fluid in organic pores, free liquid, liquid in pores, liquid in macroporosity or fractures, liquid in inorganic pores, liquid in organic pores, free gas, gas in pores, gas in macroporosity or fractures, gas in inorganic pores, gas in organic pores, free oil, oil in pores, oil in macroporosity or fractures, oil in inorganic pores, oil in organic pores, free water, water in pores, water in macroporosity or fractures, water in inorganic pores, water in organic pores, clay-associated water, clay-bound water, surface relaxation-dominated fluid, surface relaxation-dominated oil, surface relaxation-dominated water, bulk relaxation-dominated fluid, bulk relaxation-dominated oil, bulk relaxation-dominated water, bulk relaxation-dominated gas, bound fluid, bound oil, bound water, capillary-bound fluid, capillary-bound water, capillary-bound oil, bitumen, bound hydrocarbon, free hydrocarbon, and any combination thereof; Element 5: wherein assigning the poro-fluid class to the clusters includes analyzing a location of the modes on a plot of $T_1/T_2$ ratio as a function of $T_1$ and a plot of $T_1/T_2$ ratio as a function of $T_2$, or any plot of any of the modal properties; Element 6: the method further comprising: acquiring $T_1$ and $T_2$ relaxation time data for fluids in a rock sample or volume; and determining the poro-fluid classes and respective amounts of the fluids in the rock sample based on partitioned representations for the clusters; Element 7: Element 6 and wherein the rock sample is a subterranean formation or a core sample from the subterranean formation, and the method further comprises: identifying a zone of the subterranean formation for completion; Element 8: Element 6 and wherein the rock sample is a subterranean formation or a core sample from the subterranean formation, and the method further comprises: identifying a portion of the subterranean formation from where to obtain a core sample for further analysis; Element 9: Element 6 and wherein the rock sample is a subterranean formation or a core sample from the subterranean formation, and the method further comprises: determining a stimulation or completion operation to be performed on the subterranean formation; Element 10: Element 6 and wherein the rock sample is a subterranean formation or a core sample from the subterranean formation, and the method further comprises: identifying a horizontal well landing location within the subterranean formation; Element 11: 6 and wherein the rock sample is a subterranean formation or a core sample from the subterranean formation, and the method further comprises: managing hydrocarbons based at least in part upon the respective amounts of the fluids in the rock sample; Element 12: Element 11 and wherein managing hydrocarbons comprises one or more of: (a) identifying a zone of the subterranean formation for completion, and causing one or more completion operations to be carried out on the identified zone; (b) identifying a portion of the subterranean formation from where to obtain a core sample for further analysis, and obtaining one or more core samples from the identified portion; (c) causing a simulation or completion operation to be carried out on the subterranean formation; and/or (d) identifying a horizontal well landing location within the subterranean formation, and causing a horizontal well to be drilled to the identified landing location; Element 13: wherein the plurality of samples comprises a plurality of core samples from a subterranean formation; Element 14: wherein the NMR $T_1$-$T_2$ data from a plurality of samples comprises NMR logging data for fluids in a subterranean formation; Element 15: wherein the plurality of samples comprise a synthetic core sample; and Element 16: the method further comprising: performing a NMR logging operation for a subterranean formation; analyzing data from a first portion of the NMR logging operation in real-time to produce the partitioned representations; and determining the poro-fluid classes and respective amounts of the fluids in the subterranean formation for a second portion of the NMR logging operation based on the partitioned representations.

Another nonlimiting example embodiment is a computing device comprising: a processor; a memory coupled to the processor; and instructions provided to the memory, wherein the instructions are executable by the processor to perform the method according to any of the foregoing method embodiments.

Examples of combinations of elements for the nonlimiting example method embodiment and/or the nonlimiting example computing device embodiment may include, but are not limited to, two or more of Elements 1-5 in combination; one or more of Elements 1-5 in combination with Element 6 and optionally one or more of Elements 7-10; one or more of Elements 1-5 in combination with one or more of Elements 13-16; and Element 11 and optionally Element 12 in combination with one or more of Elements 1-10.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

Examples

Figure 2A:
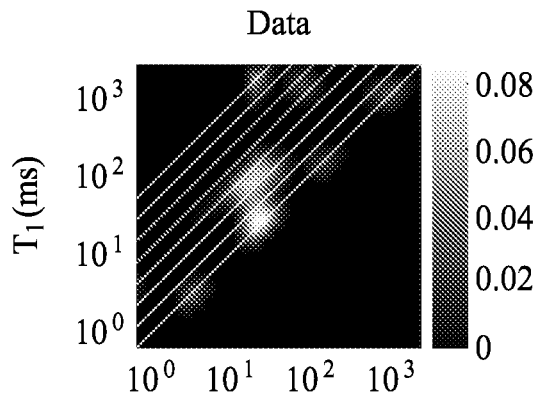
FIG. 2(A) is a data $T_1$-$T_2$ cross-plot.

FIG. 2(A) is a $T_1$-$T_2$ cross-plot of NMR data collected from a subterranean rock or core sample. The diagonal lines are generic lines that correspond to specific absolute values of $T_1/T_2$ ratios.

The $T_1$-$T_2$ cross-plot was deconvolved using multimodal Gaussian deconvolution or decomposition achieved with a regularized nonlinear Levenberg-Marquartz inversion. The 2D Gaussian mixture of multimodal poro-fluids representation is $$G_{t,2D} = \sum_i^I A_i \exp\left(-\frac{1}{2} x_i^T \sigma_i^{-1} x_i\right) \quad \text{(Eq. 1)}$$

where $A_i$ is the peak poro-amplitude;

$$x_i = \begin{bmatrix} x_1 - \mu_{i1} \\ x_2 - \mu_{i2} \end{bmatrix}$$

where $x_1$ and $x_2$ are logarithm of $T_1$ and $T_2$ relaxations, and are Gaussian mean centers in logarithm of $T_1$ and $T_2$ dimensions, respectively; superscript T represents matrix transpose notation;

$$\sigma_i = \begin{bmatrix} \sigma_{i1,1}^2 & \sigma_{i1,2}^2 \\ \sigma_{i2,1}^2 & \sigma_{i2,2}^2 \end{bmatrix}$$

is the shape covariance matrix which must be symmetric and positive definite; and subscript i represents the i-th Gaussian poro-fluid mode for which $i=1, 2, \ldots, I$. In this example $I=9$ from automatic local maxima and inflections identification.

It follows, in a Gaussian representation, that fractional pore volume, $\phi_i$, associated with mode i is given as $$\phi_i = A_i \sqrt{\frac{4\pi^2}{|\sigma_i^{-1}|}} \quad \text{(Eq. 2)}$$

where total fluid-filled NMR porosity, $\phi_t$, is $$\phi_t = \sum_i^I \phi_i \quad \text{(Eq. 3)}$$

Therefore, the multimodal poro-fluid properties or modal properties vector (m) to be solved, for I number of Gaussian modes, is $$m = [A_i, \mu_{i1}, \mu_{i2}, \sigma_{i1,1}^2, \sigma_{i1,2}^2, \sigma_{i2,2}^2, \ldots, A_I, \mu_{I1}, \mu_{I2}, \sigma_{I1,1}^2, \sigma_{I1,2}^2, \sigma_{I2,2}^2]^T \quad \text{(Eq. 4)}$$

The nonlinear regularized Levenberg-Marquartz inversion solution is implemented as an iterative gradient-based minimization of following model, toward solving $\Delta m^k$:

$$\left\| \begin{bmatrix} J(m^k) \\ \lambda^k I \end{bmatrix} \Delta m^k + \begin{bmatrix} e^k \\ \lambda^k I m^k \end{bmatrix} \right\|_2^2 \quad \text{(Eq. 5)}$$

where k represents the k-th nonlinear iteration; $J(m^k)$ is the k-th Jacobian matrix obtained from the derivative of Eqs. 1-3 with respect to $m^k$; $e^k$ is the k-th misfit vector between Eqs. 1-3 and the actual $T_1$-$T_2$ cross-plot and its total fluid-filled porosity; $m^{k+1} = m^k + \Delta m^k$, where $m^0$ is an initial guess obtained by local maxima or inflection of the $T_1$-$T_2$ cross-plot; $\lambda^k$ is the scalar regularization parameter per k-th iteration; and I is an identity matrix. The misfit (e) includes Eqs. 2 and 3 such as to impose a total pore volume constraint.

Selection of $\lambda^k$ is based on the minimum $e^k$ from multiple singular value decomposition (SVD) Tikhonov regularization methods (see Aster et al. 2005) computed in parallel, specifically but not limited to, (1) general cross-validation, (2) general cross-validation of damped SVD, (3) general cross-validation of truncated SVD, (4) l-curve corner, (5) l-curve corner of damped SVD, (6) l-curve corner of truncated SVD, and (7) variance of $e^k$. This novel approach of multi-regularization method guarantees a fast convergence to a stable solution because the path to minimum possible misfit is selected at every k-th iteration. The iteration is terminated when $\|e^k\|_2^2 - \|e^{k-1}\|_2^2 < \varepsilon$, $\forall k > \epsilon$, where $\varepsilon$ is threshold for change in misfit and $\epsilon$ is minimum number of iterations.

Figure 2B:
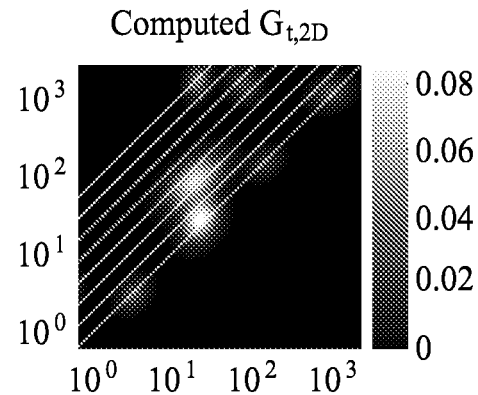
FIG. 2(B) is the recombined approximate $T_1$-$T_2$ cross-plot representation of FIG. 2(A).
Figure 2C:
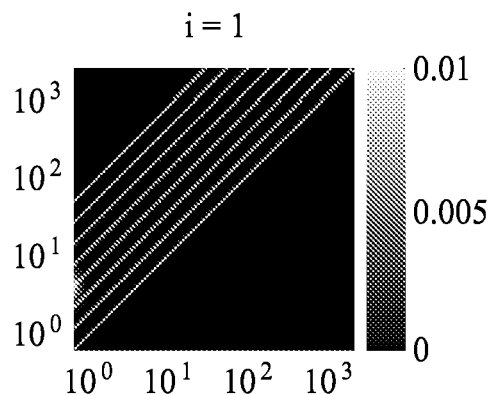
FIGS. 2(C)-2(K) are the plots of the deconvolved individual modes of FIG. 2(A).
Figure 2D:
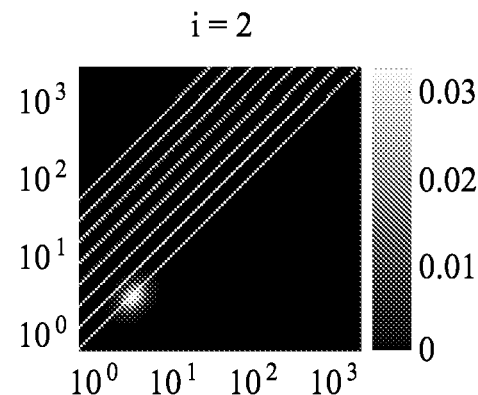
Figure 2E:
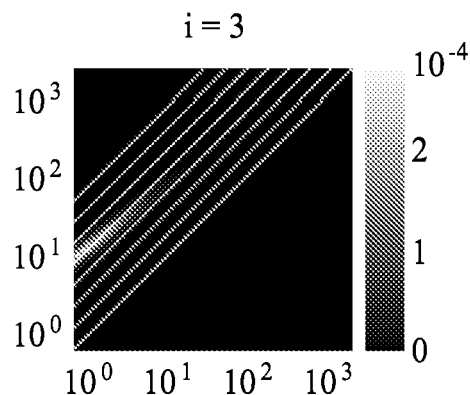
Figure 2F:
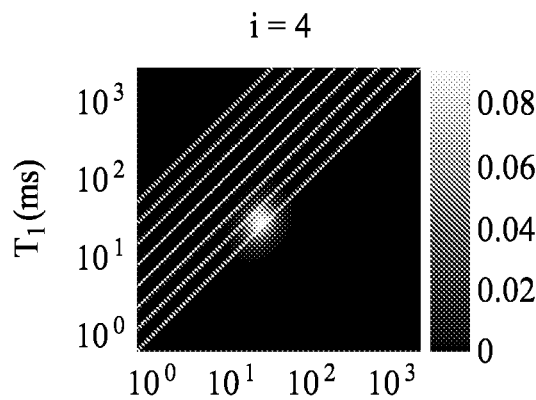
Figure 2G:
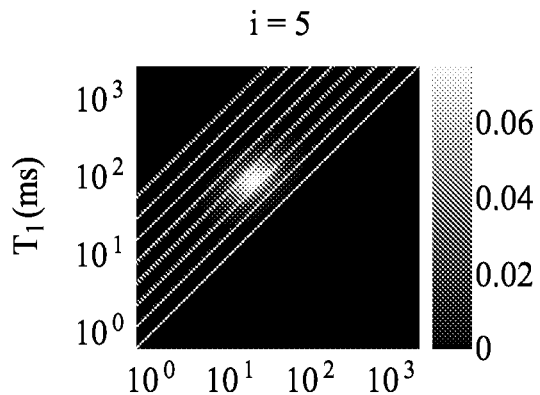
Figure 2H:
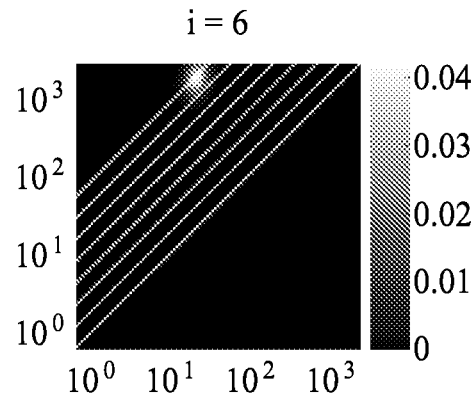
Figure 2I:
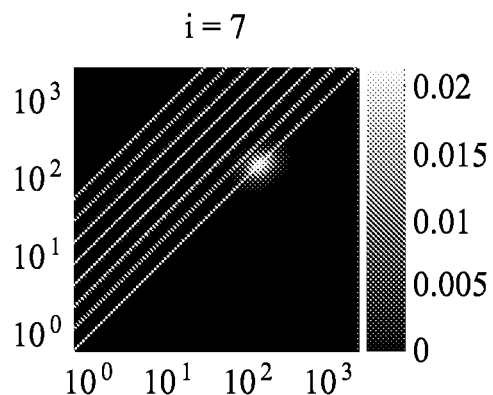
Figure 2J:
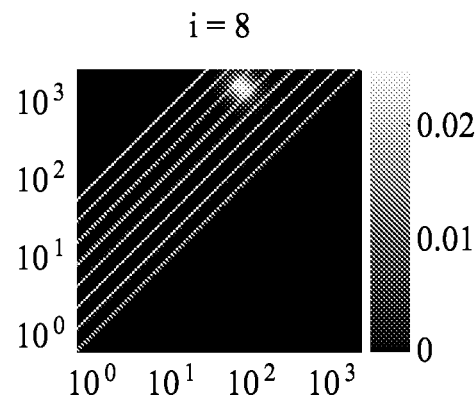
Figure 2K:
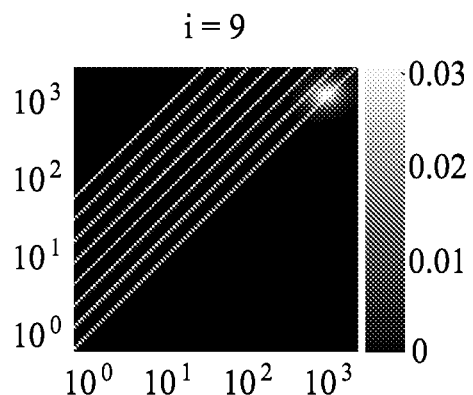

The individual component modes deconvolved by this method are illustrated in FIGS. 2(C)-2(K). FIG. 2(B) is the recombined approximate $T_1$-$T_2$ cross-plot representation of actual $T_1$-$T_2$ in FIG. 2(A).

In this example, the NPPM analysis describes nine different poro-fluid modes that represent distinct combinations of fluid-types in pore-sizes. The total porosity, $\phi_t$, was determined to be 9.74 p.u. Table 1 summarizes the nine NPPM modes where the poro-fluid class designation is based on the peak $T_{1i}$, peak $T_{2i}$, and peak $T_{1i}/T_{2i}$ ratio. In this example, the multimodal decomposition required less than 0.01 second of CPU time, which illustrates the advantageous speed of the NPPM analyses described herein.

TABLE 1

| Mode number, i | $A_i$, poro-amplitude (p.u.) | Peak $T1_i$ (ms) | Peak $T2_i$ (ms) | Peak $T1_i/T2_i$ ratio | $\phi_i$, fractional pore volume (p.u.) | $S_i$, fractional saturations (%) | $\sigma_{i1,1}^2$ | $\sigma_{i2,2}^2$ | $\sigma_{i1,2}^2 = \sigma_{i2,1}^2$ | poro-fluid class |
|---|---|---|---|---|---|---|---|---|---|---|
| 1 | 0.0124 | 3.98 | 0.53 | 7.54 | 0.06 | 0.62 | 0.0014 | 0.0155 | 0.0001 | Organic matter porosity |
| 2 | 0.0346 | 2.87 | 3.11 | 0.92 | 0.56 | 5.75 | 0.0153 | 0.0171 | 0.0066 | Clay-associated water |

TABLE 1-continued

| Mode number, i | $A_i$, poro-amplitude (p.u.) | Peak $T1_i$ (ms) | Peak $T2_i$ (ms) | Peak $T1_i/T2_i$ ratio | $\phi_i$, fractional pore volume (p.u.) | $S_i$, fractional saturations (%) | $\sigma_{i1,1}^2$ | $\sigma_{i2,2}^2$ | $\sigma_{i1,2}^2 = \sigma_{i2,1}^2$ | poro-fluid class |
|---|---|---|---|---|---|---|---|---|---|---|
| 3 | 0.0003 | 10.98 | 0.58 | 18.77 | 0.01 | 0.1 | 0.3143 | 0.1995 | 0.2474 | Oil in organic pores |
| 4 | 0.0926 | 32.99 | 26.69 | 1.24 | 2.93 | 30.08 | 0.0251 | 0.0360 | 0.0092 | Water in inorganic pores |
| 5 | 0.0775 | 116.09 | 22.28 | 5.21 | 3.86 | 39.63 | 0.0599 | 0.0489 | 0.0298 | Moveable oil in inorganic pores |
| 6 | 0.0448 | 2978.01 | 25.17 | 118.34 | 0.68 | 6.98 | 0.0098 | 0.0228 | 0.0040 | Macro-porosity or fractures |
| 7 | 0.0222 | 204.23 | 213.04 | 0.96 | 0.39 | 4.01 | 0.0194 | 0.0153 | 0.0068 | Free water |
| 8 | 0.0253 | 2567.95 | 110.72 | 23.19 | 0.53 | 5.44 | 0.0191 | 0.0197 | −0.0014 | Gas in fractures or macro-pores |
| 9 | 0.0318 | 1988.38 | 1795.13 | 1.11 | 0.72 | 7.39 | 0.0276 | 0.0168 | 0.0059 | Free water or free gas |

Figure 2L:
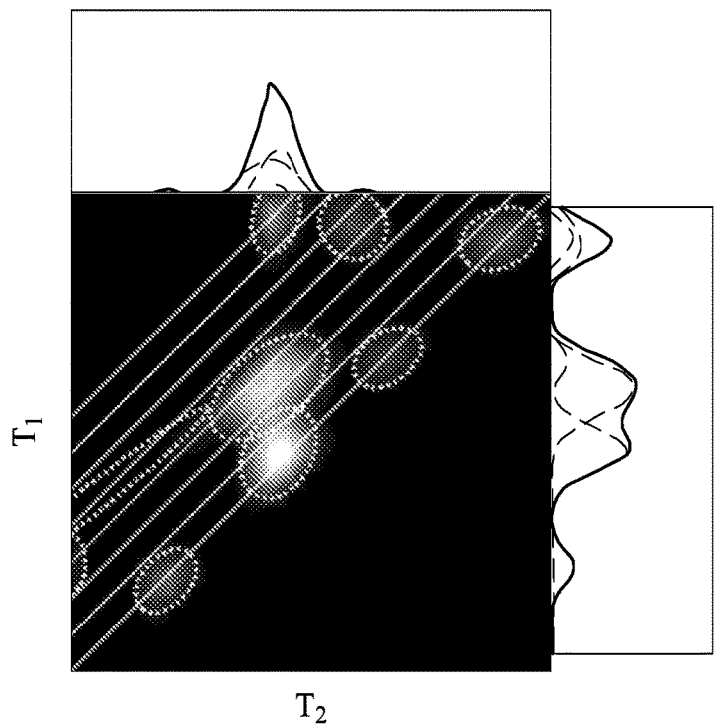
FIG. 2(L) is FIG. 2(A) with overlaid ovular markings to highlight the nine deconvolved modes with, along their respective axes, amplitude as a function of T1 or T2 plot for deconvolved modes (dashed line) and the summation (solid line).

FIG. 2(L) is the data $T_1$-$T_2$ cross-plot with overlaid ovular markings to highlight the 9 deconvolved modes with, along their respective axes, amplitude as a function of $T_1$ or $T_2$ plot for deconvolved modes (dashed line) and the summation (solid line). This illustrates the overlap in the distribution of the various modes if only an amplitude is considered as a function of $T_1$ or $T_2$ and not the cross-plot.

Figure 2M:
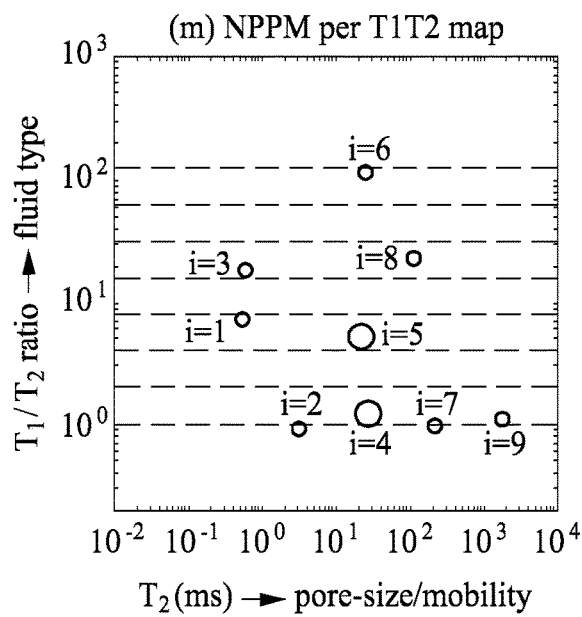
FIGS. 2(M)-2(N) are the modes of FIGS. 2(C)-2(K) replotted as $T_1/T_2$ ratio as a function of $T_2$ and $T_1$, respectively.
Figure 2N:
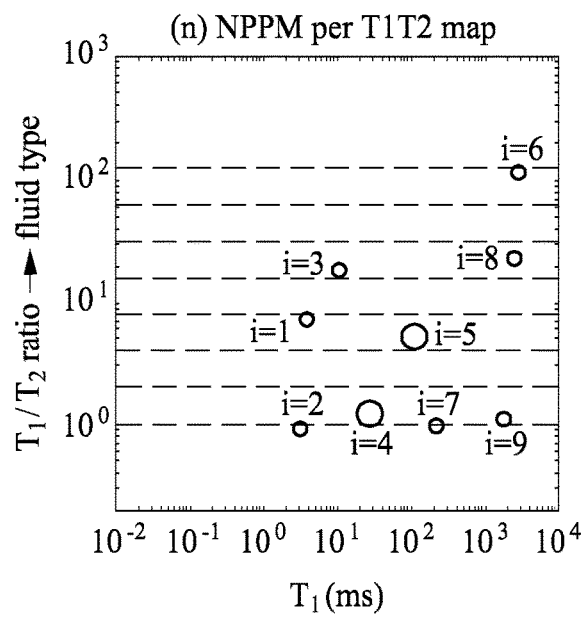

The nine modes (i=1, 2, . . . , 9) are replotted in FIGS. 2(M)-2(N) for modal properties of the $T_1/T_2$ ratio as a function of $T_2$ and $T_1$, respectively, where size of markers is relatively proportional to modal fluid volume for visualization purposes. The $T_1/T_2$ ratio provides insight regarding the fluid type, the $T_2$ data provides insight regarding pore size in which the fluid is located and mobility of the fluid, the $T_1$ data provides insight regard fluid type, wettability, and other relaxation effects, and the sum of the amplitude for the different modes provides insight regarding the fluid volume that the mode accounts for.

Figures 4A, 4B:
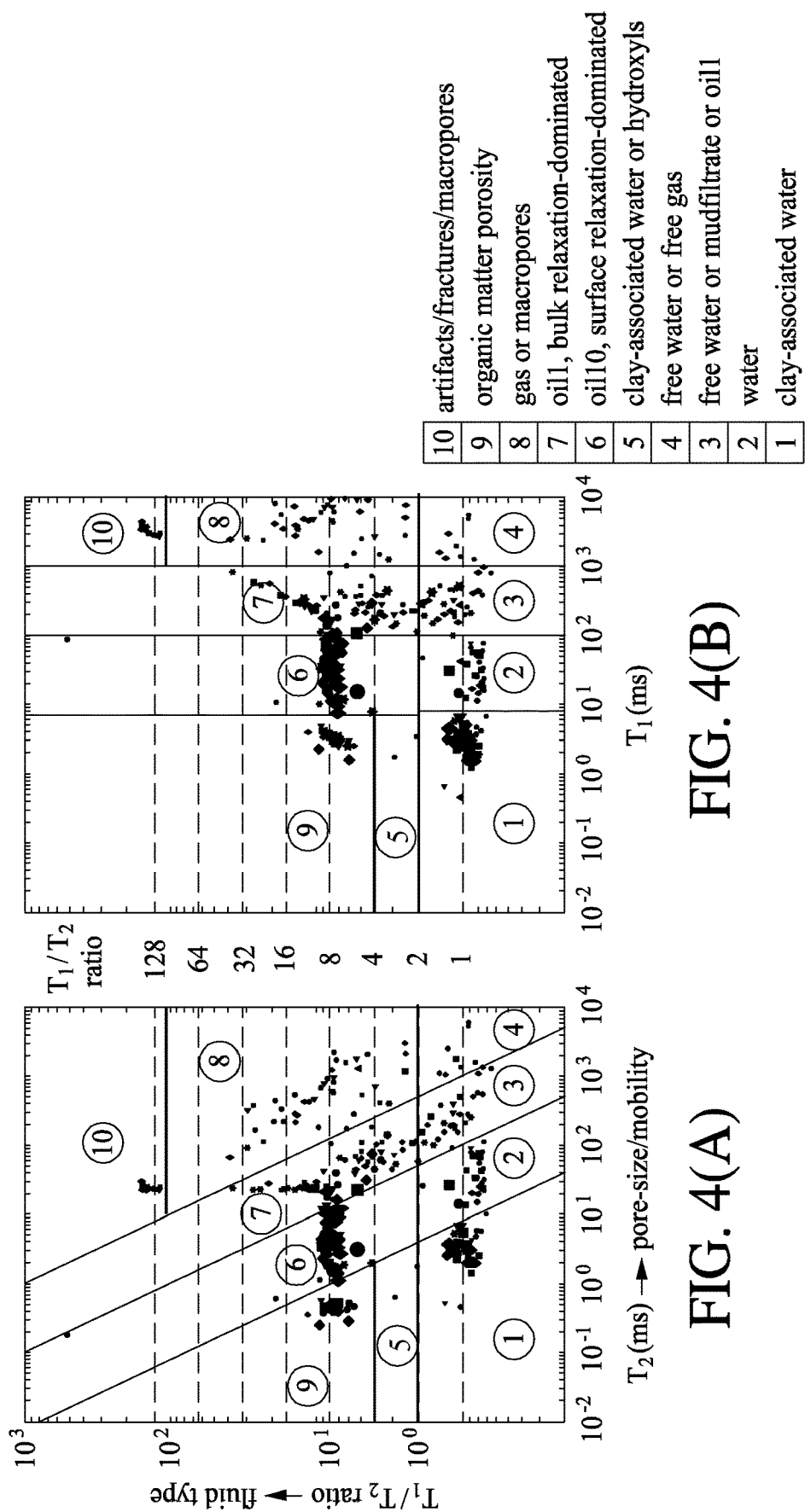
Figure 4C:
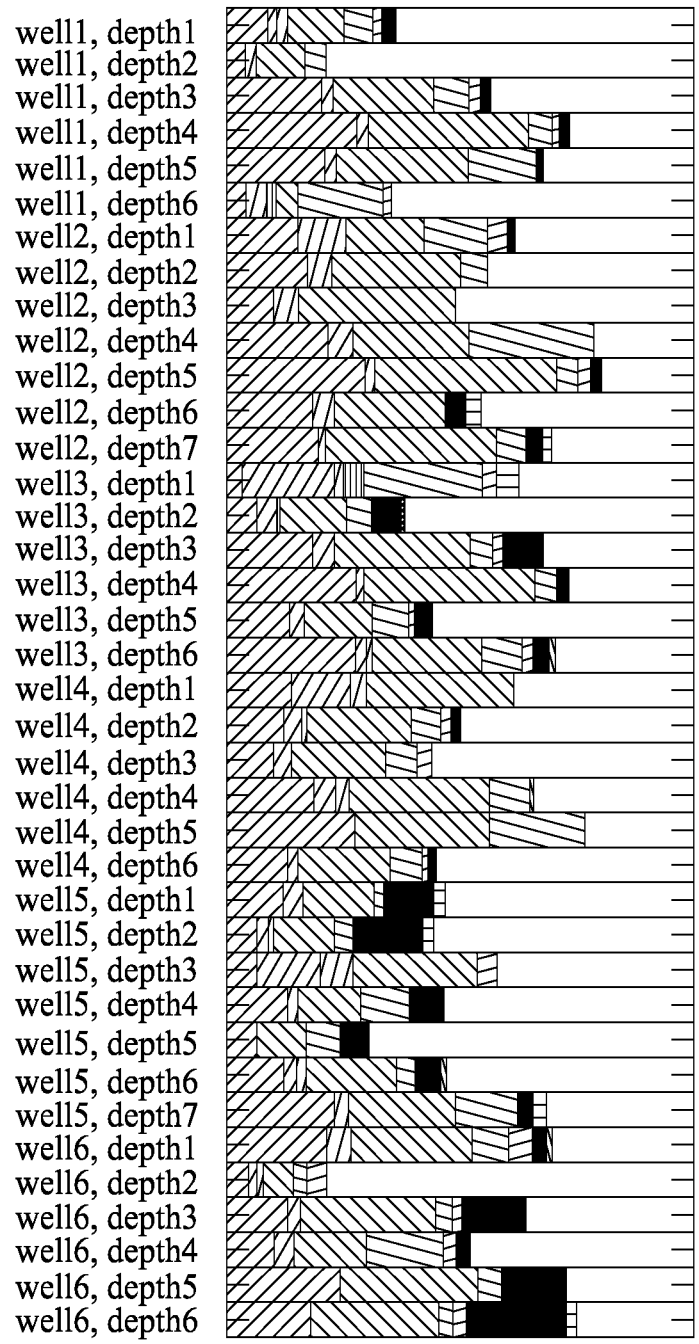
FIG. 4(C) and FIG. 4(D) are modal pore volumes cumulated to total fluid-filled porosity.
Figure 4D:
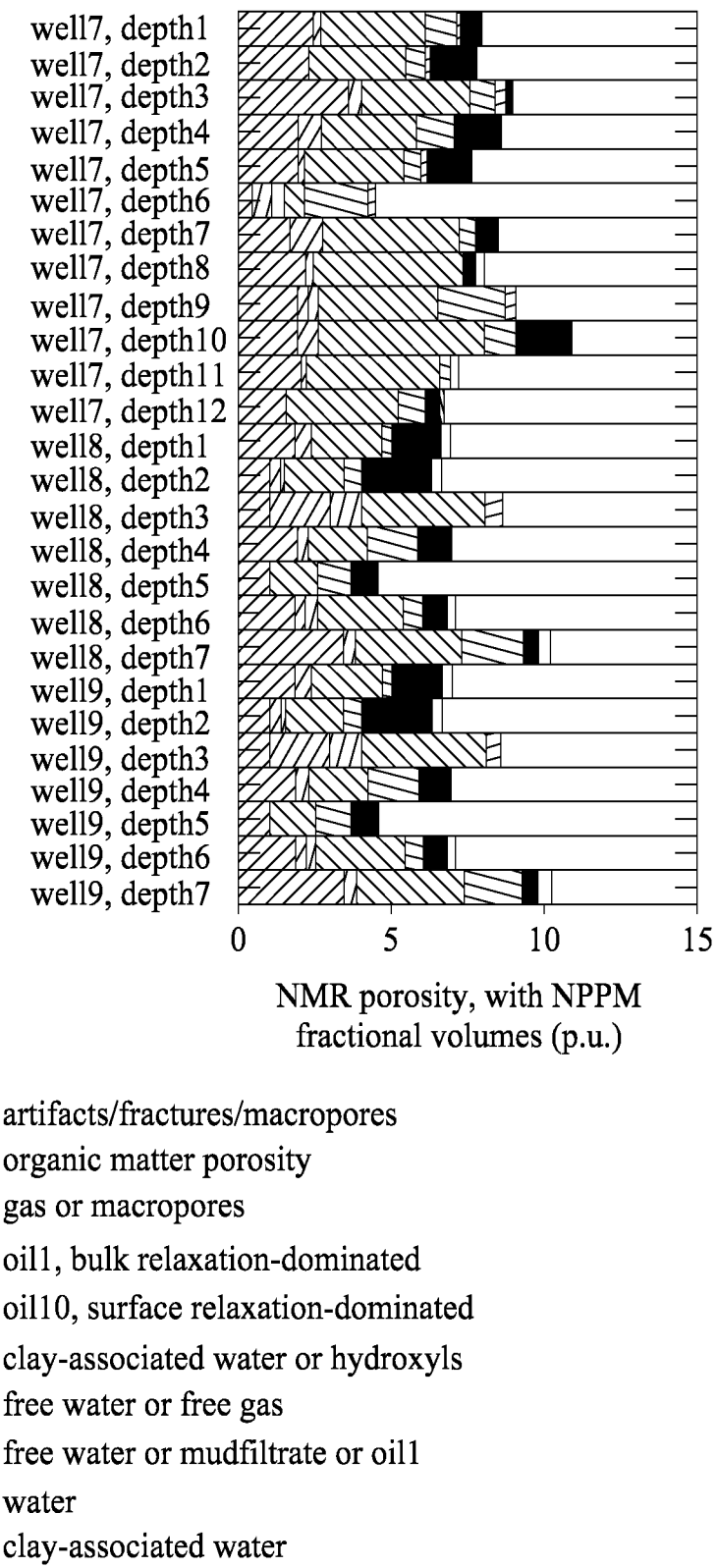

Data for several rock samples at different depths from multiple wells in the same basin were treated the same as above. The data for each rock sample were overlaid and are illustrated in FIGS. 3(A)-3(B) for the $T_1/T_2$ ratio as a function of $T_2$ and $T_1$, respectively. By visual inspection, clusters of the modal properties clearly emerge for samples in this basin. Furthermore, cluster analysis is performed to obtain most representative cluster associations of modal properties. In this example, ten cluster associations are obtained, i.e., j=1, 2, . . . , 10, and hence ten corresponding poro-fluid classes can be so defined by one skilled in the art at identifying poro-fluid class definitions based on mean or moment of the poro-fluid clusters' $T_1$, $T_2$, and $T_1/T_2$ ratio. While ten classes are illustrated in this example, any number of classes (e.g., one to twelve or more) can be defined. From these, the partitioned representations (e.g., regions, regimes, and boundaries) of the two graphs of $T_1/T_2$ ratio as a function of $T_2$ and $T_1$ can be assigned, see FIGS. 4(A)-4(B), respectively with poro-fluid class definitions in FIG. 4(D). Then, analysis of fluid type and pore volume for other rock samples from said basin, field, or wells can be analyzed using the regions and boundaries set out in FIGS. 4(A)-4(B) in the same manner as FIG. 4(C) and FIG. 4(D).

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method of improving production of hydrocarbons, comprising:
    identifying modes in NMR $T_1$-$T_2$ data from a plurality of samples with a multimodal deconvolution or decomposition with regularized nonlinear inversion, the multimodal deconvolution or decomposition with regularized nonlinear inversion being independent of a priori known databases of fluid sources;
    deriving a modal properties vector comprising modal properties for each of the modes;
    performing a cluster analysis of the modes to identify clusters;
    assigning a poro-fluid class to the clusters based on one or more of the modal properties of the modes in each of the clusters;
    deriving partitioned representations for the clusters based on the cluster analysis; and
    identifying potential hydrocarbon-bearing formations in the subsurface region based on the derived partitioned representations.

2. The method of claim 1, wherein the multimodal deconvolution or decomposition is selected from the group consisting of Gaussian, Lorentzian, Voigt, exponentially modified Gaussian, and any variation thereof.

3. The method of claim 1, wherein the regularized nonlinear inversion is selected from the group consisting of Gauss-Newton inversion, Landweber inversion, Levenberg-Marquartz inversion, Occam's inversion, and any variation thereof.

4. The method of claim 1, wherein the nonlinear regularization inversion is an iterative calculation of multiple regularizations where the regularization in each iteration having a minimum misfit proceeds to the next iteration.

5. The method of claim 1, wherein the poro-fluid classes are selected from the group consisting of free fluid, fluid in pores, fluid in macroporosity or fractures, fluid in inorganic pores, fluid in organic pores, free liquid, liquid in pores, liquid in macroporosity or fractures, liquid in inorganic pores, liquid in organic pores, free gas, gas in pores, gas in macroporosity or fractures, gas in inorganic pores, gas in organic pores, free oil, oil in pores, oil in macroporosity or fractures, oil in inorganic pores, oil in organic pores, free water, water in pores, water in macroporosity or fractures, water in inorganic pores, water in organic pores, clay-associated water, clay-bound water, surface relaxation-dominated fluid, surface relaxation-dominated oil, surface relaxation-dominated water, bulk relaxation-dominated fluid, bulk relaxation-dominated oil, bulk relaxation-dominated water, bulk relaxation-dominated gas, bound fluid, bound oil, bound water, capillary-bound fluid, capillary-bound water, capillary-bound oil, bitumen, bound hydrocarbon, free hydrocarbon, and any combination thereof.

6. The method of claim 1, wherein assigning the poro-fluid class to the clusters includes analyzing a location of the modes on a plot of $T_1/T_2$ ratio as a function of $T_1$ and a plot of $T_1/T_2$ ratio as a function of $T_2$.

7. The method of claim 1 further comprising:
    acquiring $T_1$ and $T_2$ relaxation time data for fluids in a rock sample; and
    determining the poro-fluid classes and respective amounts of the fluids in the rock sample based on partitioned representations for the clusters.

8. The method of claim 7, wherein the rock sample is a subterranean formation or a core sample from the subterranean formation, and the method further comprises:
    managing hydrocarbons based at least in part upon the respective amounts of the fluids in the rock sample.

9. The method of claim 8, wherein managing hydrocarbons comprises one or more of:
    identifying a zone of the subterranean formation for completion, and causing one or more completion operations to be carried out on the identified zone;
    identifying a portion of the subterranean formation from where to obtain a core sample for further analysis, and obtaining one or more core samples from the identified portion;
    causing a simulation or completion operation to be carried out on the subterranean formation; and/or
    identifying a horizontal well landing location within the subterranean formation, and causing a horizontal well to be drilled to the identified landing location.

10. The method of claim 1, wherein the plurality of samples comprises a plurality of core samples from a subterranean formation.

11. The method of claim 1, wherein the NMR $T_1$-$T_2$ data from a plurality of samples comprises NMR logging data for fluids in a subterranean formation.

12. The method of claim 1, wherein the plurality of samples comprise a synthetic core sample.

13. The method of claim 1 further comprising:
    performing a NMR logging operation for a subterranean formation;
    analyzing data from a first portion of the NMR logging operation in real-time to produce the partitioned representations; and
    determining the poro-fluid classes and respective amounts of the fluids in the subterranean formation for a second portion of the NMR logging operation based on the partitioned representations.

14. A computing device for improving the production of hydrocarbons, comprising:
    a processor;
    a memory coupled to the processor; and
    instructions provided to the memory, wherein the instructions are executable by the processor and are configured to:
        identify modes in NMR $T_1$-$T_2$ data from a plurality of samples with a multimodal deconvolution or decomposition with regularized nonlinear inversion, the multimodal deconvolution or decomposition with regularized nonlinear inversion being independent of a priori known databases of fluid sources;
        derive a modal properties vector comprising modal properties for each of the modes;
        perform a cluster analysis of the modes to identify clusters;
        assign a poro-fluid class to the clusters based on one or more of the modal properties of the modes in each of the clusters;
derive partitioned representations for the clusters based on the cluster analysis; and identify potential hydrocarbon-bearing formations in the subsurface region based on the derived partitioned representations.

* * * * *